United States Patent [19]

Edwards et al.

[11] Patent Number: 4,869,115

[45] Date of Patent: Sep. 26, 1989

[54] AUTOMATIC SOIL SAMPLING MACHINE

[76] Inventors: Robert D. Edwards, P.O. Box 633, Lumberton, N.C. 28359; A. Earl Smith, Rte. 1, Box 302, Hope Mills, N.C. 28348

[21] Appl. No.: 205,744

[22] Filed: Jun. 13, 1988

[51] Int. Cl.⁴ .................... G01N 1/04; A01B 33/02
[52] U.S. Cl. .................... 73/864.31; 172/78; 172/112; 172/120; 172/123; 73/864.41
[58] Field of Search .......... 172/22, 21, 15, 76, 172/42, 43, 113, 112, 120, 123, 118, 78, 79, 19, 20, 16; 37/94; 73/864.41, 864; 175/20

[56] References Cited

U.S. PATENT DOCUMENTS

| Re. 30,901 | 4/1982 | Boxrud | 172/22 X |
|---|---|---|---|
| 1,455,046 | 5/1923 | Downie et al. | 172/41 X |
| 2,658,290 | 11/1953 | Pierce | 172/120 X |
| 3,122,111 | 2/1964 | Taylor, Sr. | 172/604 X |
| 3,464,504 | 9/1969 | Stange | 73/864.45 X |
| 3,559,748 | 2/1971 | Shelton | 172/604 |
| 3,625,296 | 12/1971 | Mabry | 73/864.31 X |
| 4,148,362 | 4/1979 | Orth | 172/112 X |
| 4,356,734 | 11/1982 | Ivancsics | 73/864.41 X |
| 4,538,688 | 9/1985 | Szucs et al. | 172/604 X |

FOREIGN PATENT DOCUMENTS

| 0252906 | 5/1963 | Australia | 172/21 |
|---|---|---|---|
| 1272610 | 7/1968 | Fed. Rep. of Germany | 172/604 |

Primary Examiner—Richard J. Johnson
Assistant Examiner—Jeffrey L. Thompson
Attorney, Agent, or Firm—Rhodes, Coats & Bennett

[57] ABSTRACT

The present invention entails an automatic soil sampling machine that is pulled through the field by a prime mover. A disk is utilized and is power driven by an internal combustion engine or other power source. About the outer circumference of the disk there is provided structure that effectively engages the soil as the disk is powered therethrough and flings the soil upwardly out of the ground into a rooster tail airborne configuration. A catching basket or container is mounted on the soil sampling machine and catches the soil particles being flung from the ground.

18 Claims, 3 Drawing Sheets

AUTOMATIC SOIL SAMPLING MACHINE

FIELD OF THE INVENTION

The present invention relates to soil sampling, and more particularly to an automatic continuous soil sampling machine of the type that is powered through a field and which is designed to automatically sample the soil in the process.

BACKGROUND OF THE INVENTION

Soil sampling is a most important practice among farmers. It is of the utmost importance for the farmer to understand and appreciate what is the best fertilizer composition for certain crops. This is particularly important with respect to high cash crops and crops that are especially susceptible to disease or to other factors such as nematodes. For example, a sweet potato farmer will rely on soil sampling to enable him to choose the optimum fertilizer composition and to determine if the soil needs to be treated or conditioned for such conditions or nematodes.

In the past, soil sampling has been a very laborious and time consuming undertaking. For a four to five acre tract, it would be recommended to take approximately 15 to 20 separate soil samples. This means that the individual taking the soil samples would have to walk over the entire four to five acre tract and to take samples at appropriately spaced areas within the tract. Unfortunately, the time and trouble of this has discouraged many farmers from undertaking and carrying out a most valuable soil sampling program.

There have been devised automatic soil sampling machines. One such sampling machine is shown in U.S. Pat. No. Re. 30,901. There the disclosure shows a cylindrical drum with a series of soil sampling probes extending radially therefrom. As the device is pulled through the field, the soil sampling projections or the probes are extended through the ground and soil is compacted therein. During the rotating process the soil received within the soil probes is transferred into the container. This type of machine is deemed unsatisfactory because of problems inherent in loading the soil probes and then transferring that loaded compacted soil core into the inner disposed chamber. It is very difficult to envision a machine of this design being efficient and effective in certain soils especially soils that are hard, clayey and are filled with rock and stone.

There has been and continues to be a need for a fully automatic continuous soil sampling machine that is relatively simple in design and which is effective and efficient in performing a continuous and automatic soil sampling operation.

SUMMARY AND OBJECTS OF THE INVENTION

The present invention entails an automatic soil sampling machine that is designed to be pulled through the field and to continuously and automatically retrieve soil samples. In particular, the soil sampling machine of the present invention is designed t be pulled behind a prim mover and includes a disk that is driven by a power source and which engages and extends into the ground. In one design, the disk includes an outer fluted structure that engages soil particles and lumps and because the disk is driven, flings soil out of the ground up into the air in a somewhat rooster tail configuration. Mounted on the soil sampling machine is a catching container that follows the disk and which catches soil particles flung from the ground by the disk. By simply making a series of crossing paths through a field, a representative soil sample can be quickly and efficiently taken.

It is therefore an object of the present invention to provide an automatic soil sampling machine that saves time and labor.

Another object of the present invention is to provide an automatic and continuous soil sampling machine that is easy to use, and which is rugged and dependable.

A further object of the present invention resides in the provision of an automatic soil sampling machine that is compatable with a wide range of soil types.

Still a further object of the present invention resides in the provision of an automatic and continuous soil sampling machine that is capable of obtaining a most representative soil sample.

Still a further object of the present invention resides in the provision of a soil sample machine that operates and works on the basic principal of penetrating the earth and continuously engaging soil particles or small lumps and flinging the soil from the earth such that it assumes a rooster tail airborne type configuration and catching a certain portion of that soil to form a soil sample.

Another object of the present invention resides in the provision of an automatic soil sampling machine of the character referred to above that can be easily adjusted for various soil penetration depths.

Other objects and advantages of the present invention will become apparent and obvious from a study of the following description and the accompanying drawings which are merely illustrative of such invention.

DETAILED DESCRIPTION OF THE INVENTION

Figure 1:
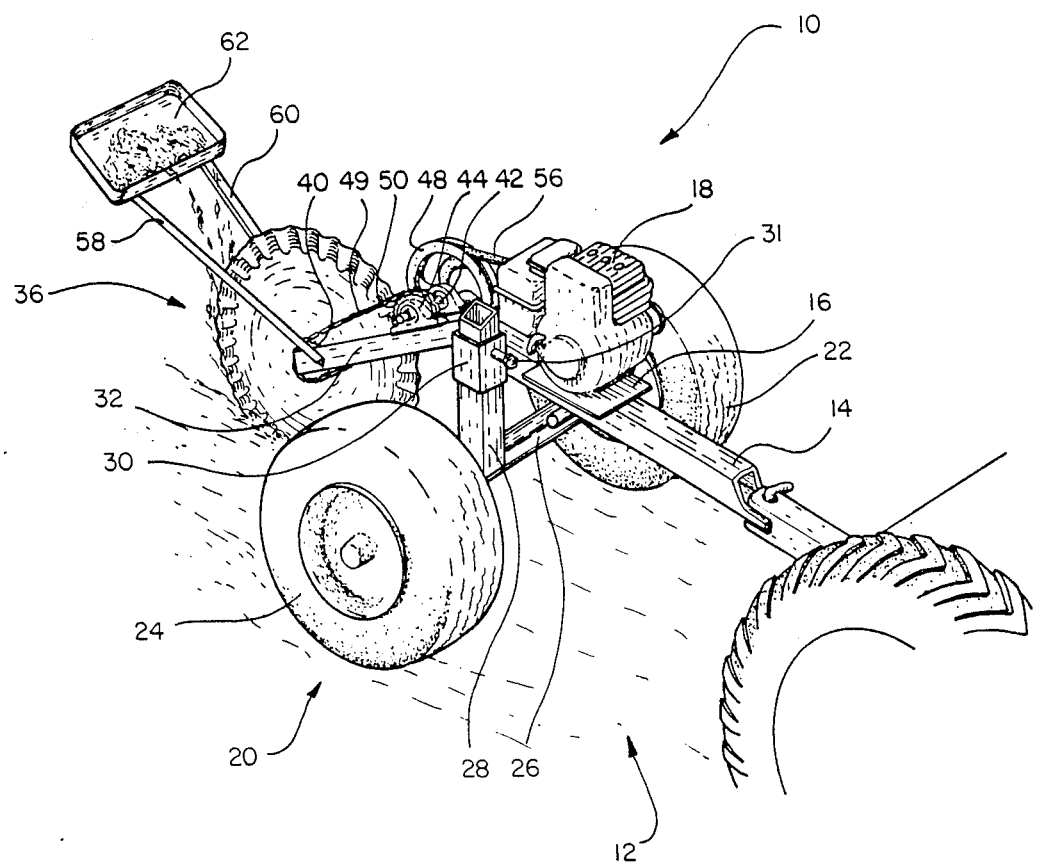
FIG. 1 is perspective view of the automatic soil sampling machine of the present invention.

With further reference to the drawings, the soil sampling machine of the present invention is shown therein and indicated generally by the numeral 10. Viewing the soil sampling machine 10 in detail it is seen that the same comprises a main frame 12 that includes an elongated beam 14. About the front of beam 14 is a clevis or other attaching structure for enabling the soil sampling machine to be attached directly to a truck, tractor, all-terrain vehicle, or the like.

Mounted intermediately on the beam 14 is an engine mounting plate 16. Engine mounting plate 16 receives and supports an internal combustion engine 18 securely stationed thereon.

The rear portion of support beam 14 is supported by a rear wheel assembly 20 including a pair of wheels 22 and 24 and a transverse axle 26. The height of the beam 14 can be adjusted with respect to the wheels 22 and 24 and axle 26 through a vertical support member 28 which is adjustably received within a collar or insert 30. Note that the collar 30 includes a bolt 31 that can be selectively secured or tightened down onto the vertical member 28 extending through the collar or insert 30. It is therefore seen by selectively moving the vertical member 28 up and down within the collar or insert 30, the height of support beam 14 can be readily adjusted.

Extending from the rear end of support beam 14 is a pair of support arms 32 and 34, the support arms being laterally spaced. Rotatively mounted within the lower end of support arms 32 and 34 is a soil sampling disk indicated generally by the numeral 36. It is seen that disk 36 is secured to a shaft 38 that is rotatively journaled between support arms 32 and 34. Also note the presence of a drive sprocket 40 that is secured to shaft 38 and as will be understood from subsequent portions of this disclosure, serves to drive the same.

Disposed about the upper portion of arms 32 and 34 is a jack shaft 42 which is rotatively mounted between a pair of laterally spaced bearing block assemblies 44 and 46. The jack shaft 42 is rotatively journaled within the bearing block assemblies 44 and 46 and has a drive sheave 48 secured to an outer end thereof. Secured to jack shaft 42 intermediately between the bearing assemblies is a second drive sprocket 50.

Internal combustion engine 18 is provided with an output drive shaft 52 that includes a drive sheave 54 thereon. Sheaves 48 and 54 are drivingly interconnected by one or more belt drives 56 that are trained around the respective sheaves. Sprockets 40 and 50 are drivingly interconnected by a chain 49.

Secured to the lower end of the respective arms 32 and 34 is a pair of basket support members 58 and 60. Each basket support member is pivotally mounted to the arms such that it can be rotatively adjusted. Note the provision of a tightening bolt assembly that enables the respective basket support arms 58 and 60 to be securely stationed in any desired position.

Secured to the basket support arms 58 and 60 is a catching and retaining soil bin or container 62. Container 62 can be of any size or shape.

Figure 2:
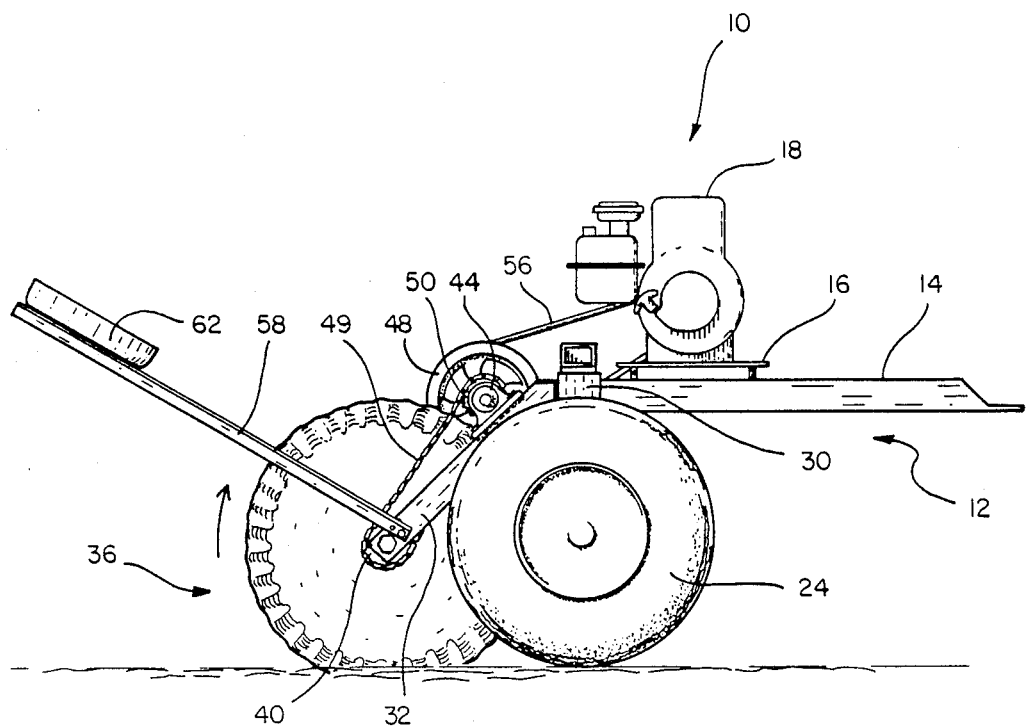
FIG. 2 is a side elevational view of the automatic soil sampling machine of the present invention.
Figure 3:
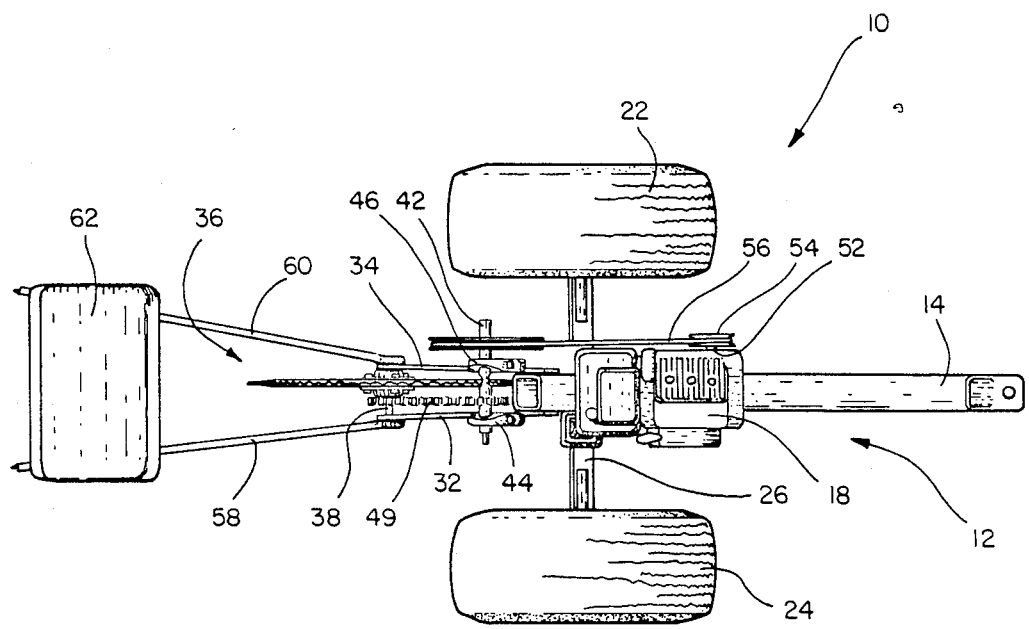
FIG. 3 is a top plan view of the automatic soil sampling machine of the present invention.

Now with reference to the soil sampling disk 36, it is seen in FIGS. 1-3 that the disk 36 disclosed therein includes a fluted outer circumference around both sides of the disk adjacent the outer edge thereof. This fluted structure serves to engage the soil and during the soil sampling operation to fling soil particles back into a rooster tail configuration where the soil falls into the soil receiving container 62.

Figure 4:
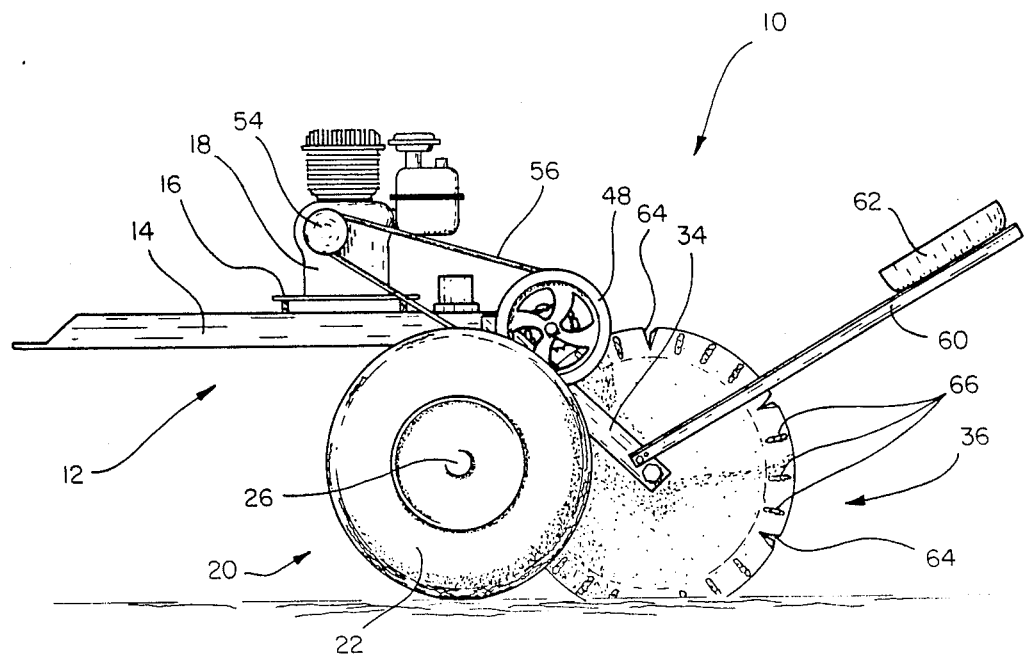
FIG. 4 is a side elevational view of the automatic soil sampling machine of the present invention shown with a soil engaging disk of an alternate design.
Figures 5, 6:
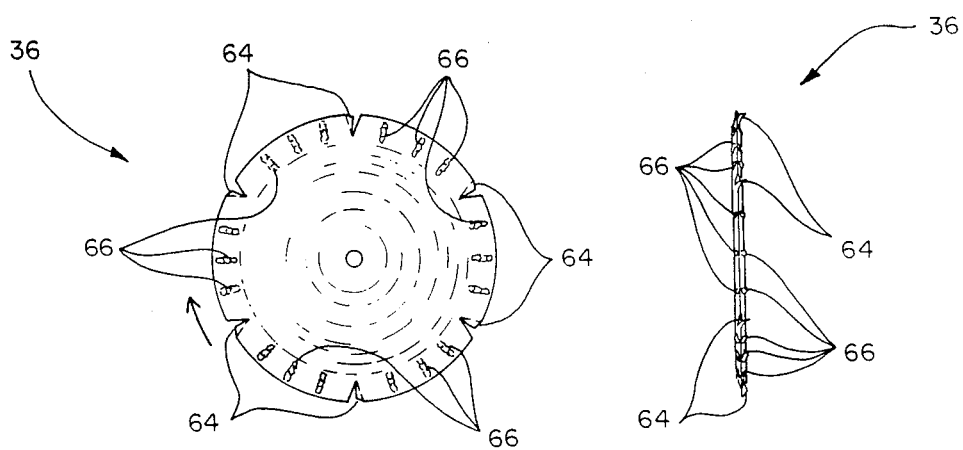
FIG. 5 is a side elevational view of the alternate disk.
FIG. 6 is a side elevational view of the alternate disk design viewing the edge of the disk.

Now turning to FIGS. 4-6, there is shown therein an alternate soil sampling disk 36. In this alternate design the terminal edge of the disk is formed with the series of sawtooth-like indentions 64 at selected intervals around the disk. The sawtooth indentions help and assist the blade in engaging and cutting through soils, especially certain hard to penetrate soils that may be the clay type or contain rock and stone. In addition, about the outer circumference, on each side of the disk, there is provided a series of radial beads or ribs 66 that are circumferentially spaced.

In operating this soil sampling machine, the same is pulled through the field and during the process the internal combustion engine is powered. The height of the support beam 14 is adjusted with respect to the rear wheel assembly 20 such that the disk 36 penetrates the earth a selected distance. Generally, the disk 36 will be driven in the direction of travel which in the case of the illustration shown in FIG. 2 would be clockwise. As the soil sampling machine moves through the field, the disk 36 will engage and penetrate the soil. As the blade is driven, the fluted or beaded outer surface will engage the soil and as the disk 36 turns the fluted or beaded surface will fling small soil particles up from the ground and into the container 62.

In practice, say for example a field that includes four to five acres, the individual taking the soil sample may simply traverse the field in a crossing configuration. That would supply sufficient soil particles to give an adequate and fair representative soil sample. Once this has been concluded, the soil is mixed within the container and then transferred into smaller containers for analyzation.

From the foregoing discussion, it is seen that the soil sampling machine of the present invention presents a very efficient and effective soil sampling machine. Clearly the labor savings is substantial and the automatic features of the soil sampling machine eliminates human error and gives a very accurate representative soil sample.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An automatic and continuous soil sampling machine comprising:
    (a) a wheel supported frame structure adapted to move through a field during a soil sampling operation; and
    (b) soil sampling means for penetrating the ground and flinging samples of soil from the ground into and through the air to where the soil samples are caught; said soil sampling means comprising:
        a disk rotatively mounted on the frame structure and adapted to penetrate downwardly into the ground during a soil sampling operation;
        soil particle flinging means carried by the disk for engaging and flinging soil particles upwardly from the ground;
        drive means for rotatively driving the disk as the frame structure is pulled through the field such that the soil flinging means carried by the disk engages soil particles within the ground and flings them upwardly and out of the ground in such a manner that the flung soil particles become airborne; and
        a soil catcher carried by the soil sampling machine spaced rearwardly of said disk for catching and collecting a portion of the airborne soil particles while permitting the remaining particles to fall to the ground.

2. The automatic and continuous soil sampling machine of claim 1 wherein said drive means for rotatively driving the disk includes means for driving the disk such that the speed of the outer periphery of the disk is substantially greater than the ground speed of the main frame structure.

3. The automatic and continuous soil sampling machine of claim 2 wherein the drive means for rotatively driving the disk includes a power source and means operatively interconnecting the disk and the power source for rotatively driving the disk.

4. The automatic and continuous soil sampling machine of claim 3 wherein the disk is rotatively driven in the same general direction as the movement of the soil sampling machine.

5. The automatic soil sampling machine of claim 1 wherein the frame structure includes a pair of wheels and wherein there is provided means for adjusting the height of the disk with respect to the wheels so as to vary the penetrating depth of the disk.

6. The automatic soil sampling machine of claim 5 wherein the frame structure includes a main elongated front frame and a pair of laterally spaced arms extending generally downwardly from the rear portion of the front frame, and wherein the disk is rotatively mounted between the laterally spaced rear arms.

7. The automatic and continuous soil sampling machine of claim 3 wherein there is provided a flexible drive means interconnecting the rotating disk and the power source.

8. The automatic soil sampling machine of claim 1 wherein said soil catcher is mounted generally rearwardly of the rotating disk.

9. The automatic soil sampling machine of claim 8 wherein there is provided a pair of adjustable arms that are secured to the frame structure and which extend generally rearwardly therefrom for supporting the soil catcher.

10. The automatic soil sampling machine of claim 9 wherein the arms supporting the soil catcher are pivotally mounted such that the position of the soil catcher can be adjusted relative to the disk.

11. The automatic soil sampling machine of claim 1 wherein the outer circumference of the disk includes a fluted configuration that engages and flings the soil particles.

12. The automatic and continuous soil sampling machine of claim 1 wherein the outer circumference of the rotating disk includes a series of circumferentially spaced cut-outs formed within the disk to assist the same in penetrating the earth.

13. The automatic soil sampling machine of claim 1 wherein the rotating disk includes a plurality of elongated projections that extend along at least one side of the disk about an outer circumferential area and wherein the elongated projections are generally radially oriented on the disk.

14. A method of continuously and automatically obtaining soil samples from a field comprising the steps of: pulling a main frame structure having a rotating disk mounted thereon across the fields; engaging the earth with the rotating disk; rotatively driving the disk in a selective direction; engaging soil particles within the ground with the disk as the disk is rotated and flinging the soil particles upwardly out of the ground such that they become airborne; and catching a portion of the flung airborne soil particles at a point rearwardly of the disk as the main frame moves through the field while permitting the remaining soil particles to fall to the ground.

15. The method of claim 14 including the step of rotatively driving the outer periphery of the disk a speed greater than the ground speed of the frame structure.

16. The method claim 14 including the step of adjusting the position of the rotating disk with respect to the ground engaging wheel supporting the main frame structure so as to adjust the depth of penetration of the disk.

17. The method of claim 14 including the step of providing projections on the disk about the outer periphery thereof and engaging soil particles with the projections as the disk is rotatively driven.

18. A pull-type automatic and continuous soil sampling machine comprising a main frame structure having a pair of wheels supporting the main frame structure, the main frame structure including a front frame having means for attaching the frame structure to a prime mover and a rear frame structure extending rearwardly from the front frame structure; the rear frame structure including a pair of laterally spaced apart arms; soil sampling means mounted to the main frame structure for penetrating the ground, flinging particles of soil from the ground into and through the air, and catching a portion of the airborne soil particles; said soil sampling means including a relatively thin disk rotatively mounted between the pair of arms forming a part of the rear main frame structure; a jack shaft rotatively journaled on the main frame structure; a flexible drive assembly operatively interconnected between the jack shaft and the rotating disk for driving the same; drive means operatively connected to the jack shaft for driving the same which results in the disk being rotatively driven; soil flinging elements formed on the outer circumference of the disk for engaging soil particles as the disk is rotated through the ground and for flinging the soil particles generally upwardly and out of the ground; a support structure extending generally rearwardly from the rotating disk; a soil catcher secured to the support structure and disposed generally rearwardly of the rotating disk for catching and collecting a portion of the soil particles that are flung upwardly and out of the ground by the driven rotating disk while the remaining soil particles fall to the ground; and means for adjusting the position of the rotating disk with respect to the support wheels of the main frame structure such that the depth of penetration of the disk can be adjusted.

* * * * *